(12) United States Patent
Gan

(10) Patent No.: US 7,851,156 B2
(45) Date of Patent: Dec. 14, 2010

(54) SCINTILLATION PROXIMITY ASSAY FOR MEASURING POLYMERASE ACTIVITY

(75) Inventor: Qing-Fen Gan, Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 88 days.

(21) Appl. No.: 11/635,826

(22) Filed: Dec. 8, 2006

(65) Prior Publication Data

US 2007/0134707 A1 Jun. 14, 2007

Related U.S. Application Data

(60) Provisional application No. 60/748,786, filed on Dec. 9, 2005.

(51) Int. Cl.
*C12Q 1/68* (2006.01)
*C12P 19/34* (2006.01)

(52) U.S. Cl. .......................................... 435/6; 435/91.2

(58) Field of Classification Search .................. None
See application file for complete search history.

(56) References Cited

U.S. PATENT DOCUMENTS

| 4,568,649 | A | 2/1986 | Bertoglio-Matte |
| 5,665,562 | A | 9/1997 | Cook |
| 5,861,318 | A | 1/1999 | Elhammer |
| 5,972,595 | A | 10/1999 | Kasila et al. |
| 6,114,132 | A | 9/2000 | Desmarais et al. |
| 6,475,751 | B2 | 11/2002 | Reynolds et al. |
| 2002/0015678 | A1 | 2/2002 | Yuan et al. |
| 2004/0110126 | A1* | 6/2004 | Kukolj et al. ............... 435/5 |

OTHER PUBLICATIONS

Yang et al., "PolC-Type Polymerase III of Strepococcus pyogenes and Its use in Screening for Chemical Inhibitors," Analytical Biochemsitry, 2002, vol. 304, pp. 110-116.*
Taylor et al., "Kinetic and Mutational Analysis of Human Immunodeficiency Virus Type 1 Reverse Transcriptase Inhibition by Inophyllums, a Novel Class of Non-nucleoside Inhibitors," J. Biol. Chem., 1994, vol. 269, No. 9, pp. 6325-6331.*
Wu et al. (Analytical Biochemistry, 1997, vol. 245, p. 226-230).*
Skorey et al. (Analytical Biochemistry, 2001, 291:269-278).*
Bochkarev et al. (Nature, 1997, 385(9):176-181).*
Cook, N.D., "Scinitilation proximity assay: a versatile high-throughput screening technology", *Drug Discov. Today*, 1996, vol. 1 (7) pp. 287-294.
Kieft, J.S. et al., "Mechanism of ribosome recruitment by hepatitis C IRES RNA", *RNA*, 2001, 7, pp. 194-206.
Lahser, F.C. et al., "A continuous nonradioactive assay for RNA-dependent RNA polymerase activity", *Anal. Biochem.*, 2004, 325, pp. 247-254.
Lohmann, V. et al., "Biochemical and structural analysis of the NS5B RNA-dependent RNA polymerase of the hepatitis C virus", *J. Viral. Hepat.* 2000, 7, pp. 167-174.
Lohmann, V. et al., "Biochemical properties of Hepatitis C Virus NS5B RNA-dependent RNA polymerase and identification of amino acid sequence motifs essential for enzymatic activity", *J. Viral.*, 1997, 71(11), pp. 8416-8428.
McKercher, G. et al., "Specific inhibitors of HCV polymerase identified using an NS5B with lower affinity for template/primer substrate", *Nucleic Acids Res.*, 2004, 32(2), pp. 422-431.
Oh, J-W. et. al., "A recombinant Hepatitis C Virus RNA-dependent RNA polymerase capable of copying the full-length viral RNA", *J. Virol.* 1999, 73(9), pp. 7694-7702.
Pellerin, C., et al., "Internal initiation sites of de novo RNA synthesis within the hepatitis C virus polypyrimidine tract", *Biochem. Biophys. Res. Commun.*, 2002, 295, pp. 682-688.
Tomei, L. et al., "Biochemical characterization of a hepatitis C virus RNA-dependent RNA polymerase mutant lacking the C-terminal hydrophobic sequence", *J. Gen. Virol.* 2000, 81, pp. 759-767.
Zheng, W. et. al. "Miniaturization of a Hepatitis C Virus RNA Polymerase Assay Using a—102° C. Cooled CCD Camera-Based Imaging System," *Analytical Biochemistry*, 2001, vol. 290 (2), pp. 214-220.
Latour, D. et. al., "Development of a Homogeneous Scintillation Proximity Assay (SPA) for Determining Activity of HCV Polymerase and Screening for Enzyme Inhibitors," *Hepatology*, 2003, vol. 38 (4), Supplemental 1, p. 633A.

* cited by examiner

*Primary Examiner*—Stephanie K Mummert
(74) *Attorney, Agent, or Firm*—David J. Chang

(57) ABSTRACT

The present invention provides for methods of assaying the activity of a polymerase enzyme by using a Scintillation Proximity Assay (SPA) without the need of primers modified with affinity tags. The methods of the present invention can be practiced with any number of RNA and DNA polymerase enzymes.

4 Claims, 2 Drawing Sheets

SCINTILLATION PROXIMITY ASSAY FOR MEASURING POLYMERASE ACTIVITY

CROSS REFERENCE TO RELATED INVENTIONS

This application claims the benefit of priority of U.S. Provisional Patent Application Ser. No. 60/748,786 filed Dec. 9, 2005, which is incorporated herein by reference in its entirety.

FIELD OF THE INVENTION

This invention pertains to biological assays for polymerase enzymes, and more particularly to a scintillation proximity assay for measuring the activities of RNA and DNA polymerase enzymes.

BACKGROUND OF THE INVENTION

Hepatitis C virus is the leading cause of chronic liver disease throughout the world. (Boyer, N. et al. *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae: The viruses and their replication.* In: *Fields Virology*, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of-approximately 3011 amino acids, and a short 3' UTR. The 5' UTR is the most highly conserved part of the HCV genome and is important for the initiation and control of polyprotein translation. The carboxyl half of nonstructural protein 5, NS5B, contains the RNA-dependent RNA polymerase.

Currently there are a limited number of approved therapies are currently available for the treatment of HCV infection. New and existing therapeutic approaches to treating HCV and inhibition of HCV NS5B polymerase have been reviewed: R. G. Gish, *Sem. Liver. Dis.*, 1999 19:5; Di Besceglie, A. M. and Bacon, B. R., Scientific American, October: 1999 80-85; G. Lake-Bakaar, *Current and Future Therapy for Chronic Hepatitis C Virus Liver Disease, Curr. Drug Targ. Infect Dis.* 2003 3(3):247-253; P. Hoffmann et al., *Recent patents on experimental therapy for hepatitis C virus infection* (1999-2002), *Exp. Opin. Ther. Patents* 2003 13(11):1707-1723; M. P. Walker et al., *Promising Candidates for the treatment of chronic hepatitis C, Exp. Opin. investing. Drugs* 2003 12(8): 1269-1280; S.-L. Tan et al., *Hepatitis C Therapeutics: Current Status and Emerging Strategies, Nature Rev. Drug Discov.* 2002 1:867-881; J. Z. Wu and Z. Hong, *Targeting NS5B RNA-Dependent RNA Polymerase for Anti-HCV Chemotherapy, Curr. Drug Targ.—Infect. Dis.* 2003 3(3):207-219.

In vitro, the polymerase activity of HCV NS5B is dependent on an RNA template and requires either a RNA or DNA primer. A variety of in vitro assays to measure the activity of the HCV NS5B polymerase have been developed. Commonly, the standard reaction mixture consists of buffers, salts, divalent cations, reducing agents, as well as nucleoside triphosphates and an RNA template and primer. The most commonly used templates and primers are synthetic homopolymeric template/primers such as poly-adenosine monophosphate:oligo-uridine monophosphate (polyA:oligo U; see, for example, S.-E. Behrens et al., *EMBO J.* 1996 15(l):12-22, V. Lohmann et al., *J. Virol.* 1997 71(11):8416-8428).

However NS5B can also initiate in vitro RNA synthesis in a primer-independent fashion when RNA templates of heteropolymeric sequence, including sequences from the HCV genome, are used. These sequences include the internal ribosome entry site located at the 5'-untranslated region of the HCV genome (HCV IRES; Kieft et al., *RNA* 2001 7:194-206) and the 3'-untranslated region (HCV 3'-UTR; Pellerin et al., *Biochem. Biophys. Res. Comm.* 2002 295:682-688). Here, the 3'-end of the template is used as the primer and elongation proceeds from a hairpin loop via a snap-back mechanism leading to a double-stranded molecule in which template and product are covalently linked.

Scintillation proximity assay (SPA) makes use of the limited pathlength of certain electron-emitters (Hart et al., *Molecular Immunology* 1979 16:265-267; Hart, U.S. Pat. Nos. 4,271,139 and 4,382,074; and Bertoglio-Matte, U.S. Pat. No. 4,568,649). An exemplary SPA is composed of an analyte in solution, plastic beads which scintillate when exposed to electrons, and a specific binding partner (such as an antibody) bound to the beads and specific for the analyte in solution. If the analyte incorporates a radioactive label which emits electrons of relatively short pathlength, such as tritium, the plastic beads will only scintillate when suspended in solution with the radioactive analyte when the analyte is specifically bound by the binding partner and thus localized near the surface of the beads.

SPAs have been developed and exploited for a variety of analytical purposes. SPAs have been used for radioimmunoassays, competition assays, enzyme kinetic assays, studies of ligand/receptor and antigen/antibody interactions, and studies of cellular processes (see, Cook, *Drug Discovery Today* 1996 1:287-294; and Cook, U.S. Pat. No. 5,665,562). The SPAs described to date all rely on specific binding interactions, such as antibody-antigen interactions, ligand-receptor interactions, biotinylated reagents which bind to streptavidin-coated beads, chelate complex formation of the species of interest, or other interactions which rely on the precise and specific structural complementarity of binding partners. While this gives SPAs high specificity for an analyte of interest, it also requires extra steps in the preparation of reagents and the time and expense of developing a binding partner system specific to the reaction of interest. It also limits its use to those systems where specific binding partners can be found or developed. For example, specific antibodies are needed for antigen-antibody assays, specific receptors are needed for ligand-receptor assays, chelate ligands must be matched to the geometry of the ion with which they form the chelation complex. If no antibodies or receptors are available for detection of a substance, specific modification of the analyte with a member of a binding pair such as biotin-streptavidin is required.

Therefore, in order to use the standard SPA assay for measuring the activity of any polymerase enzyme, including HCV NS5B polymerase, a synthetic primer such as oligo U must be modified with an affinity tag molecule (e.g. biotin), allowed to anneal to an appropriate homopolymeric template (in this case, polyA) and reacted with SPA beads coated with a molecule which can bind to the tag molecule (e.g. streptavidin). However, it would be useful and cost-effective to develop a system whereby heteropolymeric templates with either no primers or unmodified primers can be utilized in a SPA assay to measure the activity of a polymerase enzyme.

SUMMARY OF THE INVENTION

The present invention is based on the discovery that a SPA assay can be performed to measure the activity of a polymerase enzyme using either no primers or unmodified primers by contacting the products generated from the polymerase with a SPA support structure (e.g. beads) under acidic pH. By eliminating the need to use modified primers linked with an affinity tag molecule (which, by itself, is cost-effective), the SPA assay can be performed with either nucleotide sequences which are native to a given polymerase enzyme or other heteropolymeric sequences as templates which represents a more accurate condition to measure the activity of the polymerase.

Accordingly, the present invention provides a method for assaying an activity of a polymerase enzyme by: incubating a reaction mixture comprising the polymerase enzyme, an appropriate template, and a plurality of appropriately radiolabeled and non-radiolabeled nucleotide triphosphates to provide labeled transcripts with or without an unmodified primer; contacting the labeled transcripts to a suspension of a SPA support structure at a pH ranging from about 2.0 to about 4.5; and measuring a level of scintillation that correlates with the activity of the polymerase enzyme. In another embodiment, the reaction mixture is incubated in the presence of compounds that modulate the activity of the polymerase enzyme. In a preferred embodiment, the polymerase enzyme is HCV NS5B polymerase.

The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

Definitions

Figure 1:
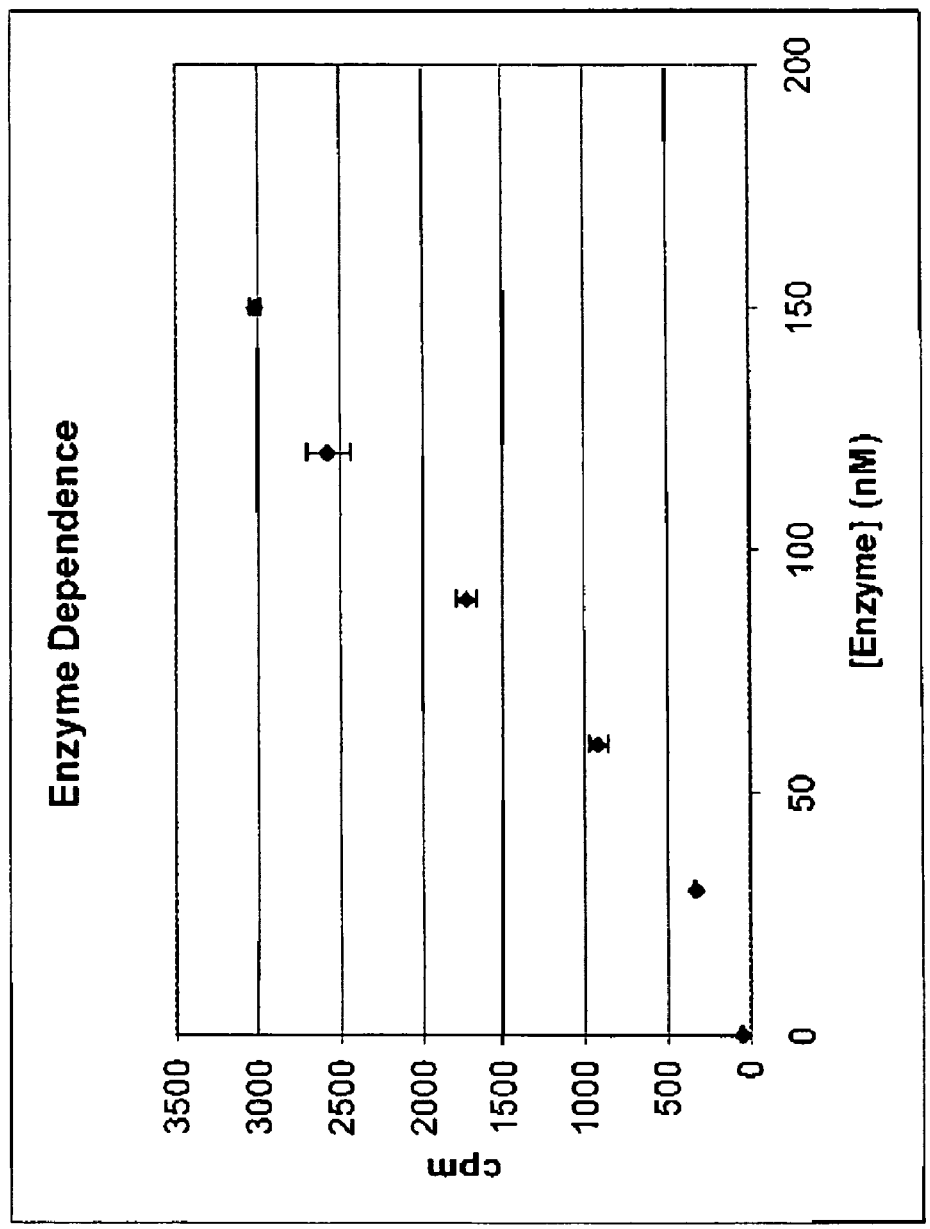
FIG. 1 Effect of NS5B polymerase concentration. The experiment was performed in a 384 well plate with NS5B concentration ranging from 0 to 160 nM. HCV IRES template at 0.26 µg/well, 1 µM CTP, GTP, ATP and 1 µCi $^3$H-UTP were present in a buffer containing 40 mM Tris (pH 8.0), 4 mM magnesium acetate and 4 mM DTT. The reactions were stopped after 2.5 hour incubation at 30° C. with a solution containing 100 mM sodium acetate (pH 3.0) and 2.3 mg/ml Protein A-PVT SPA beads.

The terms "polymerase" and "polymerase enzyme" refer to an enzyme that catalyzes the polymerization of nucleotides (i.e., the polymerase activity). Generally, the enzyme will initiate synthesis at the 3'-end of the primer annealed to a polynucleotide template sequence, and will proceed toward the 5' end of the template strand. "RNA polymerase" catalyzes the polymerization of ribonucleotides and "DNA polymerase" catalyzes the polymerization of deoxyribonucleotides. "DNA polymerases" can include "RNA-dependent DNA polymerases" which utilize RNA as the template to produce DNA strands (e.g. reverse transcriptase) as well as "DNA-dependent DNA polymerases" which utilize DNA as the template to produce DNA strands.

The term "viral polymerase" refers to a polymerase enzyme contained within the genome of a virus which catalyzes the polymerization of ribonucleotides or deoxynucleotides and allows the virus to replicate.

The term "NS5B" refers to a portion of the HCV genome located near the 3' end of the viral genome that specifies the region encoding a protein, termed the "NS5B protein", "NS5B polypeptide", "NS5B polymerase" or combinations of these terms which are used interchangeably herein. NS5B in its natural state, functions as an RNA-dependent RNA polymerase (RdRp). The nucleic acid region encoding the NS5B protein may also be referred to as the "NS5B gene". Thus, the term "NS5B" may refer to either a nucleic acid encoding the NS5B polypeptide, to an NS5B gene or to an NS5B polypeptide, or to any portions thereof, depending on the context in which the term is used. NS5B may further refer to natural allelic variants, mutants and derivatives of either NS5B nucleic acid sequences or NS5B polypeptides. The NS5B nucleic acid, NS5B gene or NS5B protein referred to is a functional polymerase, or to a non-functional polymerase that still binds to an appropriate template.

"Scintillation Proximity Assay (SPA)" refers to an homogeneous assay procedure which produces quantifiable light energy at a level which is related to the amount of radioactively labelled product in the assay medium. The light energy is produced by a scintillant which is either incorporated, or forms part of, a support structure (beads or other solid surface which can be used in the assay process). While the support structure may be coated with a capture molecule, capture molecules are not necessary for the practice of the present invention. In a direct assay, a sample containing a radiolabelled product is mixed in aqueous solution containing scintillant support structure. The radiolabelled product is caused to bind to the scintillant-containing support structure. The scintillant is activated causing emission of light, which can be detected conventionally using a scintillation counter. The amount of light produced is directly proportional to the amount of reactant bound to the surface of the support structures. Beads that are used in SPA can be microspheres, approximately 5 um in diameter, and can be made from hydrophobic polymers such as but not limited to polyacrylamide, acrylamide, agarose, polystyrene, polypropylene, polycarbonate, and polyvinyltoluene or from inorganic scintillators such as yttrium silicate. The core of the bead can be coated with a polyhydroxy film which reduces the hydrophobicity of the bead. In one embodiment, SPA beads are made from either yttrium silicate or polyvinyltoluene containing an organic scintillant such as diphenyloxazole and are commercially available from Amersham Biosciences (Piscataway, N.J.)

The isotope of an "appropriately radiolabeled" molecule refers to an isotope that has a relatively low energy beta-emission, for example tritium, or iodine-125 auger electrons. Only that portion of the sample which binds to or is in close proximity to the scintillant-containing support structure will result in scintillation events that can be counted. Unbound radiolabeled molecules will be at too great a distance from the scintillant surface to produce scintillations, the beta-decay energy being dissipated in the liquid aqueous medium.

The term "affinity tag" as used herein refers to a ligand (that is linked to a primer) whose strong affinity for a "receptor"

can be used to extract from a solution the entity to which the ligand is attached. Examples of such ligands include biotin or a derivative thereof, a histidine polypeptide, an amylose sugar moiety or a defined epitope recognizable by a specific antibody. Such "affinity tags" are preferably attached to the primer in solution and is captured by a suitable "receptor" moiety attached to a solid support.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be elongated (extended) at its 3' terminus by the addition of nucleotides by the action of a polymerase or similar activity to yield a primer elongation (extension) product. The primer may vary in length depending on the particular conditions and requirement of the application. For example, in the method of the present invention, the nucleotide or oligonucleotide primer is typically 1-24 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequences has sufficient complementarity with the sequence of the desired template strand to functionally provide a primer-template complex for the synthesis of the extension product. The term "unmodified primer" as used herein refers to a primer which is not modified or linked to an "affinity tag" molecule.

The terms "RNA synthesis" and "transcription" are used interchangeably and are defined by the specific steps taken by an RNA polymerase of: recognizing and binding to a template initiation site; priming by incorporating a first complementary nucleotide; and adding consecutively complementary nucleotides to elongate the nascent RNA chain.

The term "template" refers to an oligonucleotide of DNA, or preferably RNA, at least 50 nucleotides in length, that serves as one of the substrate for a polymerase. The sequence of a template is complementary to the sequence produced by the polymerase during transcription. An "appropriate" template for a polymerase is one which is able to serve as a substrate for a given polymerase. The term "homopolymeric template" refers to a template whose entire sequence is made up from one nucleotide, such as polyadenosine or polyguanidine. The term "heteropolymeric template" refers to a template which is not "homopolymeric" and whose sequence is made up from more than one nucleotide.

The present invention provides for methods of assaying the activity of a polymerase enzyme by using a Scintillation Proximity Assay (SPA). SPAs work by bringing a radiolabeled molecule within close proximity to a support structure's scintillant to stimulate light emission. In a first embodiment of the present invention, there is provided a method for assaying an activity of a polymerase enzyme, comprising the steps of: a) incubating a reaction mixture comprising said polymerase enzyme, an appropriate template, and a plurality of appropriately radiolabeled and non-radiolabeled nucleotide triphosphates to provide labeled transcripts, with or without an unmodified primer; b) contacting said labeled transcripts to a Scintillation Proximity Assay (SPA) support structure at a pH ranging from about 2.0 to about 4.5; and c) measuring a level of scintillation wherein said scintillation level correlates with the activity of said polymerase enzyme.

In one embodiment of the first embodiment of the present invention, the polymerase enzyme is HCV NS5B polymerase. In this assay, NS5B binds to a single stranded RNA template with or without primer and initiates de-novo synthesis of ds (double stranded) RNA. The template can either be homopolymeric, which will require a complementary primer (e.g. poly A-oligo U), or heteropolymeric which may or may not require a complementary primer. RNA templates for NS5B that do not require primers include the internal ribosome entry site located at the 5'-untranslated region of the HCV genome (HCV IRES) and the 3'-untranslated region (HCV 3'-UTR). Radiolabeled UTP and unlabeled CTP, GTP and ATP are incorporated into the double stranded helix upon polymerase-template binding. The detection of product (ds RNA) is measured by adding a fixed amount of Protein-A Poly-Vinyl Toluene (PVT) SPA Beads (in low pH) which couple to ds RNA and stop the reaction from proceeding further. Close proximity of a bead to incorporated radiolabeled UTP causes a photon to be emitted and captured by a detector. Absence of signal (photon) indicates lack of ds RNA formation via enzyme/compound blockade.

In a second embodiment of the present invention, there is provided a method for assaying an activity of a polymerase enzyme comprising the steps of: a) incubating a reaction mixture comprising said polymerase enzyme, an appropriate template, and a plurality of appropriately radiolabeled and non-radiolabeled nucleotide triphosphates to provide labeled transcripts, in the presence of one or more compounds that modulate the activity of said polymerase enzyme, with or without an unmodified primer; b) contacting said labeled transcripts to a Scintillation Proximity Assay (SPA) support structure at a pH ranging from about 2.0 to about 4.5; and c) measuring a level of scintillation wherein said scintillation level correlates with the activity of said polymerase enzyme. In a preferred embodiment of the second embodiment of the present invention, the polymerase enzyme is HCV NS5B polymerase.

The methods of the present invention can also be practiced with any number of RNA and DNA polymerase enzymes because labeled products which are generated by the polymerase (i.e. ds RNA or DNA) can be brought in proximity to the SPA support structure under acidic pH condition such that the level of scintillation correlates with the activity of the polymerase. The present invention applies to RNA and DNA polymerases from prokaryotic and eukaryotic species as well as from RNA and DNA viruses. DNA polymerases can include DNA-dependent DNA polymerases or RNA-dependent DNA polymerases such as the Human Immunodeficiency Virus reverse transcriptase (HIV-RT).

EXAMPLES

The following preparations and examples are given to enable those skilled in the art to more clearly understand and to practice the present invention. They should not be considered as limiting the scope of the invention, but merely as being illustrative and representative thereof.

Example 1

HCV NS5B RNA Polymerase Assay

N-terminally histidine tagged HCV polymerase, derived from HCV BK strain, genotype 1b (NS5B570n-BK) contains a 21 amino acid deletion at the C-terminus relative to the full-length HCV polymerase and is purified from *E. coli* strain M15. The construct containing the coding sequence of HCV BK strain amino acid residues 2421-2999 (GenBank accession number M58335) downstream of a Taq promoter expression cassette was inserted into plasmid constructs. The plasmid constructs were transformed in *E. coli* and colonies were inoculated and grown overnight in 10 L of Terrific broth (Tartoff and Hobbs) supplemented with 100 μg/mL ampicillin at 37° C. Protein expression was induced by addition of 1 mM isopropyl-β-D-thiogalactopyranoside (IPTG), when optical densities reached between 1.5 and 3.5 $OD_{600}$ and the culture was then incubated for 16- to 18 h at 22° C. NS5B570n-BK was purified to homogeneity using a three step protocol including subsequent column chromatography on Ni-NTA, SP-Sepharose HP and Superdex 75 resins.

Figure 2:
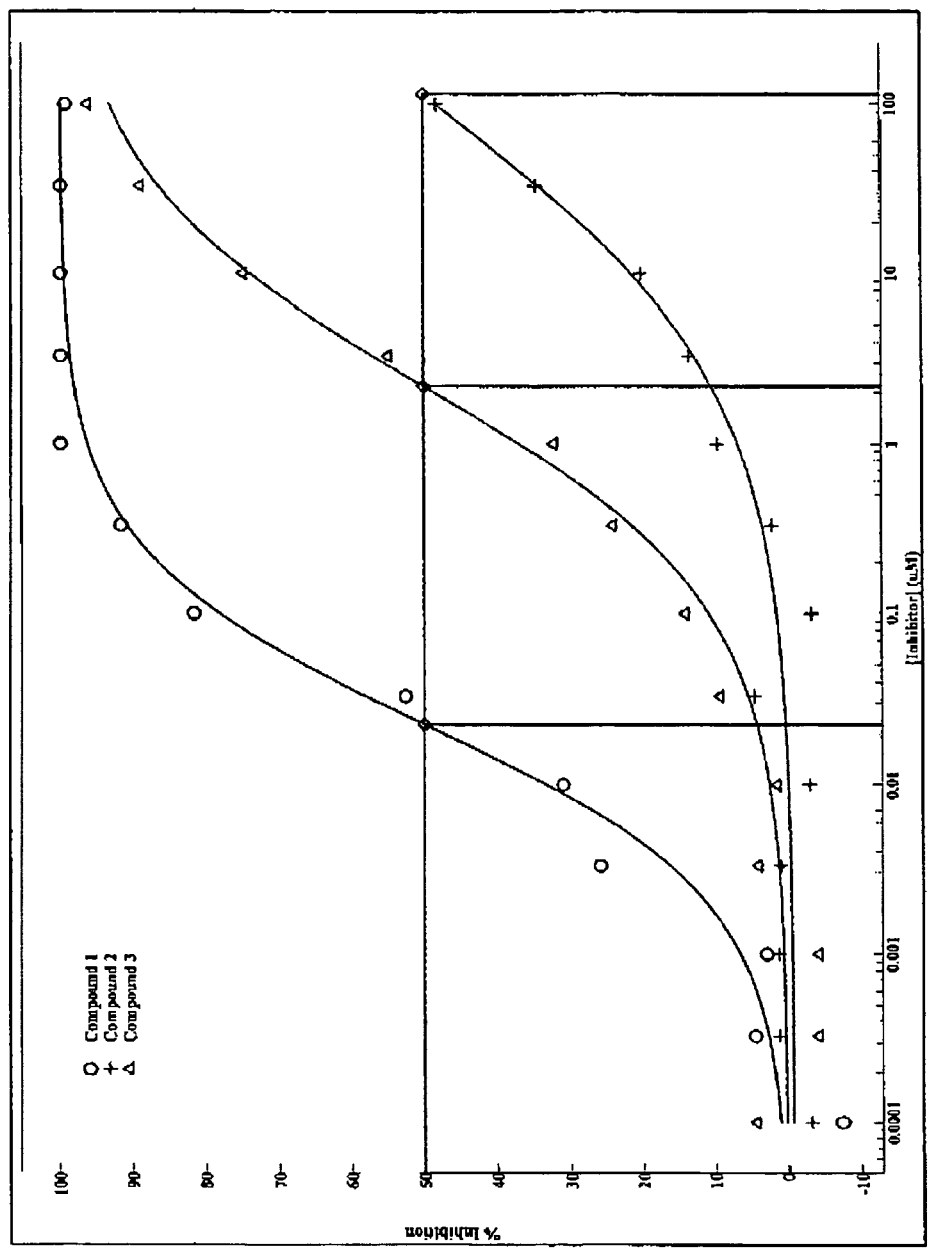
FIG. 2 Dose-response curves of known NS5B inhibitors: The experiment was performed in a 384 well plate with NS5B concentration at 0.23 µg/20 µl. HCV IRES template at 0.26 µg/20 µl, 1 µM CTP, GTP, ATP and 1 µCi $^3$H-UTP were present in a buffer containing 40 mM Tris (pH 8.0), 4 mM magnesium acetate, 4 mM DTT and 10% DMSO. The reactions were stopped after 2.5 hour incubation at 30° C. with a solution containing 100 mM sodium acetate (pH 3.0) and 2.3 mg/ml Protein A-PVT SPA beads.

NS5B Polymerase was added into a 384 well plate at various concentrations and co-incubated with a 377 nucleotide HCV IRES template sequence (SEQ ID NO:1), which contains nucleotide residues 21-371 of the HCV 5'-untranslated region from GenBank accession number AF356827, at 0.26 μg/well concentration and 1 μM CTP, GTP, ATP and 1 μCi $^3$H-UTP (Amersham TRK412, 1 mCi/ml) in a buffer containing 40 mM Tris (pH 8.0), 4 mM magnesium acetate and 4 mM DTT. In some instances, test compounds at 10 μM concentration were also added. After three hour incubation at 30° C., a solution containing 100 mM sodium acetate (pH 3.0) and 2.3 mg/ml Protein A-PVT SPA beads was added to each well. Samples were left to settle for 12 hours at room temperature. The amount of light emitted from the scintillant contained in the SPA Beads was converted to counts per minutes (CPM) on a Topcount plate reader (Perkin-Elmer). FIG. 1 shows the results of the assay under different concentrations of the NS5B Polymerase. FIG. 2 shows the results of the assay in the form of dose response curves of several known inhibitors of NS5B Polymerase.

Example 2

HIV-1 Reverse Transcriptase Assay

Recombinant reverse transcriptase (RNA-directed DNA polymerase) from HIV-1 strain can be expressed in *E. coli* and purified as described in Mizrahi et al., *Arch. Biochem. Biophys.* 1989 273:347-358. The reverse transcriptase is added into microtiter plate and mixed with 5 μg/ml poly (rA) template pre annealed to 2.5 μg/ml oligo $(dT)_{16}$ primer, and 1 μM dATP, dCTP, dGTP and 1 μCi [methyl-1'2'-$^3$H] dTTP (Amersham TRK-576) in a buffer consisting of 40 mM Tris (pH 8.0), 4 mM magnesium acetate and 4 mM DTT. Reaction is run at 37° C. for 30 min. After incubation a solution containing 100 mM sodium acetate (pH 3.0) and 2.3 mg/ml Protein A-PVT SPA beads is added to each well and the samples are treated and scintillation is detected as described in Example 1.

Example 3

*E. coli* DNA Polymerase I (Klenow) Assay

The polymerase activity of *E. coli* DNA Polymerase I Large (Klenow) Fragment which is commercially available (e.g. Invitrogen Cat. No. 18012-021) can be assayed using the methods described in Example 2 but using as template either double-stranded DNA with free 3'-hydroxyl ends (e.g. generated by DNase I digestion) and no primers or single-stranded DNA with specific or random primers.

---

What is claimed is:

1. A method for assaying an activity of a HCV NS5B polymerase enzyme, comprising the steps of:
   a) incubating a reaction mixture comprising said polymerase enzyme, a heteropolymeric template that does not require both a complementary primer and an affinity tag molecule, and a plurality of appropriately radiolabeled and non-radiolabeled nucleotide triphosphates to provide labeled transcripts;
   b) contacting said labeled transcripts to a Scintillation Proximity Assay (SPA) support structure at a pH ranging from about 2.0 to about 4.5; and
   c) measuring a level of scintillation wherein said scintillation level correlates with the activity of said polymerase enzyme.

2. The method of claim 1 wherein said heteropolymeric template is selected from the group consisting of HCV IRES and HCV 3'-UTR.

3. A method for assaying an activity of a HCV NS5B polymerase enzyme comprising the steps of:
   a) incubating a reaction mixture comprising said polymerase enzyme, a heteropolymeric template that does not require both a complementary primer and an affinity tag molecule, and a plurality of appropriately radiolabeled and non-radiolabeled nucleotide triphosphates to provide labeled transcripts, in the presence of one or more compounds that modulate the activity of said polymerase enzyme;
   b) contacting said labeled transcripts to a Scintillation Proximity Assay (SPA) support structure at a pH ranging from about 2.0 to about 4.5; and
   c) measuring a level of scintillation wherein said scintillation level correlates with the activity of said polymerase enzyme.

4. The method of claim 3 wherein said heteropolymeric template is selected from the group consisting of HCV IRES and HCV 3'-UTR.

* * * * *

SEQUENCE LISTING

```
<160> NUMBER OF SEQ ID NOS: 1

<210> SEQ ID NO 1
<211> LENGTH: 377
<212> TYPE: RNA
<213> ORGANISM: Hepatitis C virus

<400> SEQUENCE: 1
guuugguuuu cuuugagguu uaggaaucgu gcucauggug cacggucuac gagaccuccc      60
ggggcacucg caagcacccu aucaggcagu accacaaggc cuuucgcgac ccaacacuac     120
ucggcuagua gucucgcggg ggcacgccca aaucuccagg cauugagcgg guugauccaa     180
gaaaggaccc ggucguccug gcaauuccgg uguacucacc gguuccgcag accaccaugg     240
cucucccggg aggggggguc ccggaggcua cacgacacuc auacuaacgc cauggcuaga     300
cgcuuucugc gugaagacag uaguuccuca caggggagug aucuauggug gaguguucauu     360 uuuaaucaaa aauuggc                                                   377
```